(12) United States Patent
Fujinuma et al.

(10) Patent No.: US 10,859,816 B2
(45) Date of Patent: Dec. 8, 2020

(54) SCANNING-TYPE IMAGE ACQUISITION DEVICE AND SCANNING-TYPE IMAGE ACQUISITION SYSTEM

(71) Applicant: OLYMPUS CORPORATION, Tokyo (JP)

(72) Inventors: Ken Fujinuma, Tokyo (JP); Yuhei Takata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/403,830

(22) Filed: May 6, 2019

(65) Prior Publication Data

US 2019/0258050 A1 Aug. 22, 2019

Related U.S. Application Data

(63) Continuation of application No. PCT/JP2016/088496, filed on Dec. 22, 2016.

(51) Int. Cl.
*A61B 1/07* (2006.01)
*A61B 1/00* (2006.01)
(Continued)

(52) U.S. Cl.
CPC .............. *G02B 26/103* (2013.01); *A61B 1/00* (2013.01); *A61B 1/00006* (2013.01);
(Continued)

(58) Field of Classification Search
CPC .......... G02B 26/10; G02B 23/24; A61B 1/00; A61B 1/07; H04N 5/235
See application file for complete search history.

(56) References Cited

U.S. PATENT DOCUMENTS

| 2008/0165360 A1 | 7/2008 | Johnston |
| 2010/0165291 A1* | 7/2010 | Sugita ................ G01B 9/02089 |
| | | 351/206 |

(Continued)

FOREIGN PATENT DOCUMENTS

| JP | 5513897 B2 | 6/2014 |
| JP | 2014-149354 A | 8/2014 |

(Continued)

OTHER PUBLICATIONS

International Search Report dated Mar. 28, 2017 received in PCT/JP2016/088496.

*Primary Examiner* — Dave Czekaj
*Assistant Examiner* — Berteau Joisil
(74) *Attorney, Agent, or Firm* — Scully, Scott, Murphy & Presser, P.C.

(57) ABSTRACT

A scanning-type image acquisition device includes: drivers that respectively vibrate in an x direction and a y direction that are perpendicular to a longitudinal axis of an optical fiber that guides illumination light from a light source and cause a tip of the optical fiber to be spirally scanned on a subject; a drive-signal generating circuit that generates drive signals for driving the drive units; an adjustment section that adjusts the drive signals generated by the drive-signal generating circuit and generates position reference data; a photodetector that detects scattered light of the illumination light at each scanning position of an illumination light spot on the subject due to the drivers; and an image generating circuit that generates an image by arranging intensity values of the scattered light detected by the photodetector in pixels in accordance with the position reference data output from the adjustment section.

8 Claims, 11 Drawing Sheets

(51) Int. Cl.
  *G02B 26/10* (2006.01)
  *G02B 23/24* (2006.01)
  *H04N 5/235* (2006.01)
  *H04N 5/225* (2006.01)

(52) U.S. Cl.
  CPC ............ *A61B 1/00172* (2013.01); *A61B 1/07* (2013.01); *G02B 23/2423* (2013.01); *G02B 23/2469* (2013.01); *G02B 23/2484* (2013.01); *G02B 26/101* (2013.01); *H04N 5/2354* (2013.01); *H04N 2005/2255* (2013.01)

(56) References Cited

U.S. PATENT DOCUMENTS

| | | | |
|---|---|---|---|
| 2012/0025068 A1* | 2/2012 | Clench | H01J 49/164 250/282 |
| 2013/0003131 A1 | 1/2013 | Johnston | |
| 2015/0294466 A1 | 10/2015 | Johnston | |
| 2018/0303321 A1 | 10/2018 | Takata | |

FOREIGN PATENT DOCUMENTS

| | | |
|---|---|---|
| JP | 5608718 B2 | 10/2014 |
| WO | 2008/085186 A1 | 7/2008 |
| WO | 2014/020943 A1 | 2/2014 |
| WO | 2017/109958 A1 | 6/2017 |

\* cited by examiner

SCANNING-TYPE IMAGE ACQUISITION DEVICE AND SCANNING-TYPE IMAGE ACQUISITION SYSTEM

This is a continuation of International Application PCT/JP2016/088496, with an international filing date of Dec. 22, 2016, which is hereby incorporated by reference herein in its entirety.

TECHNICAL FIELD

The present invention relates to a scanning-type image acquisition device and a scanning-type image acquisition system.

BACKGROUND ART

There is a known scanning-type image acquisition device that acquires an image by vibrating, by using an actuator such as a piezoelectric element, the tip of an optical fiber that guides illumination light so that the illumination light is scanned along a predetermined trajectory on a subject and arranging the intensities of reflected light detected at respective scanning positions on the basis of information on the scanning positions (for example, refer to PTL 1).

CITATION LIST

Patent Literature

{PTL 1} The Publication of Japanese Patent No. 5513897

SUMMARY OF INVENTION

An aspect of the present invention provides a scanning-type image acquisition device that includes: drivers that respectively vibrate in an x direction and a y direction that are perpendicular to the longitudinal axis of an optical fiber that guides illumination light from a light source and cause a tip of the optical fiber to be spirally scanned on a subject, a drive-signal generating unit for generating drive signals for driving the drivers, an adjustment section that adjusts the drive signals generated by the drive-signal generating unit and generates position reference data, a photodetection unit that detects scattered light of the illumination light at each subject scanning position of an illumination light spot by the drivers; and an image generating unit that generates an image by arranging intensity values of the scattered light detected by the photodetection unit in pixels in accordance with the position reference data output from the adjustment section.

Another aspect of the present invention provides an image processing device including the scanning-type image acquisition device, an imaging unit configured to capture a projection graphic projected by the scanning-type image acquisition device, and an adjustment amount determining unit that determines an amount of adjustment by the adjustment section on the basis of an amount of deviation from the projection graphic data.

DESCRIPTION OF EMBODIMENTS

A scanning-type image acquisition device 1 according to an embodiment of the present invention will be described below with reference to the drawings.

Figure 1:
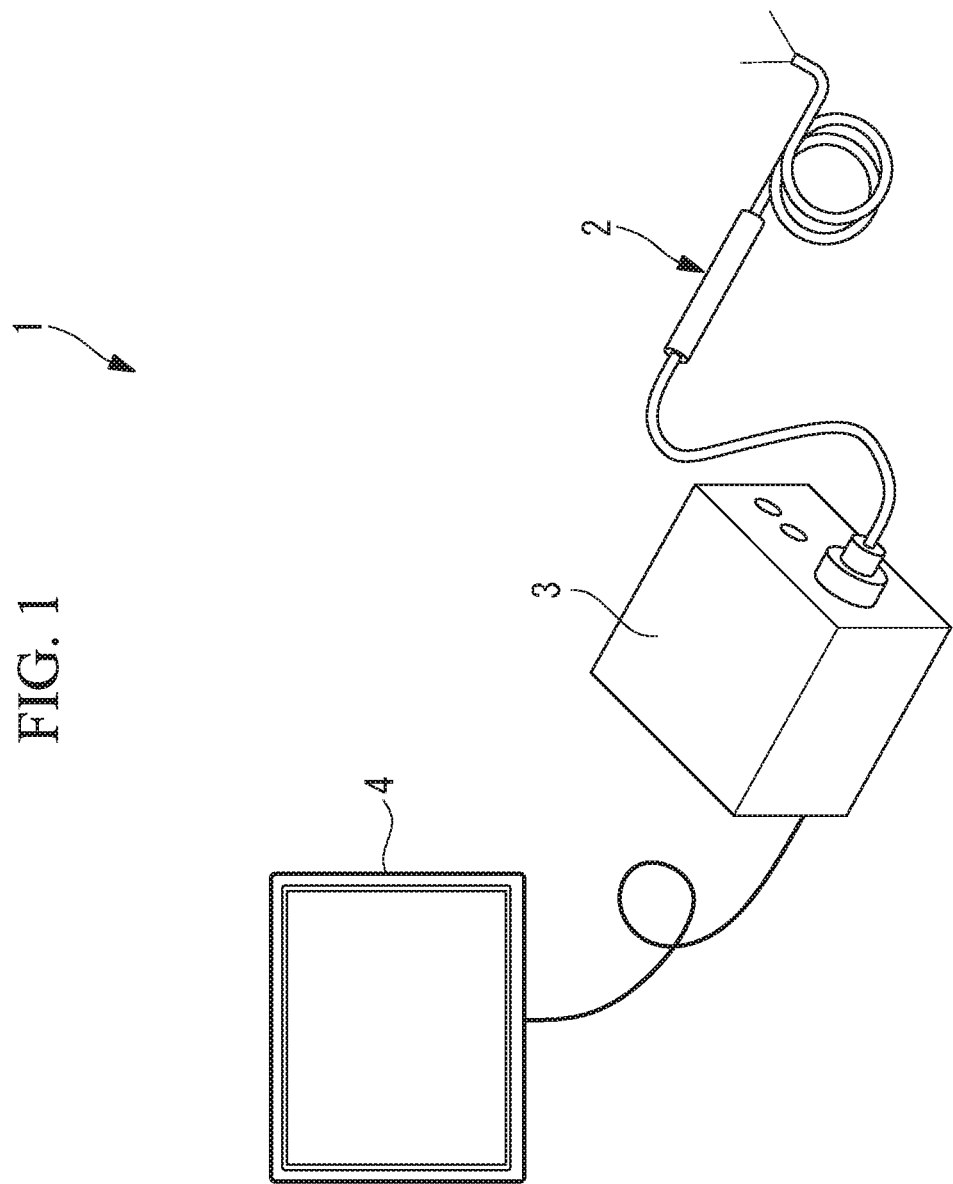
FIG. 1 is an overall configuration diagram illustrating a scanning-type image acquisition device according to an embodiment of the present invention.

The scanning-type image acquisition device 1 according to the present embodiment is a scanning-type endoscope device, and, as illustrated in FIG. 1, includes a scanning-type endoscope 2 that illuminates a subject with illumination light from a light source 9 and detects light scattered by the subject, an endoscope control device 3 that controls the scanning-type endoscope 2 and generates an image of the subject, and a monitor 4 that displays the generated image.

Figure 2:
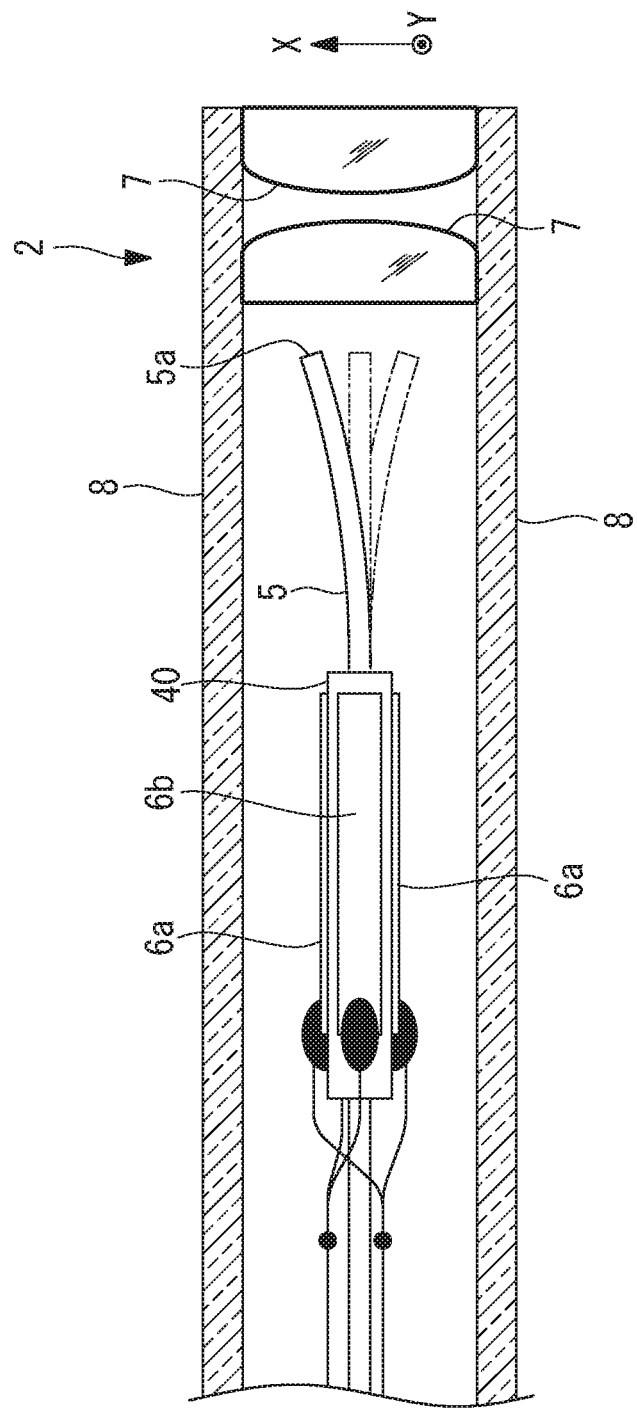
FIG. 2 is a partial vertical sectional view illustrating the internal structure of a scanning-type endoscope provided in the scanning-type image acquisition device in FIG. 2.

The scanning-type endoscope 2, as illustrated in FIG. 2, includes an optical fiber 5 for guiding illumination light from the light source 9, a ferrule 40 that has a cylindrical shape and that supports the optical fiber 5, a plurality of piezoelectric elements (drivers) 6a and 6b fixed to an outer circumferential surface of the ferrule 40, an illumination lens (optical lens) 7 for spreading out the illumination light emitted from the tip of the optical fiber 5 to illuminate the subject, and a detection fiber bundle 8 that detects light scattered from an illumination light spot on the subject.

In addition, in the scanning-type endoscope 2 described in this embodiment, two or more piezoelectric elements 6a and 6b are provided, and a tip 5a of the optical fiber 5 is made to vibrate in the x direction and the y direction, which are perpendicular to the longitudinal axis of the optical fiber 5.

The ferrule 40 is formed of a member capable of transmitting vibrations and transmits vibrations from the piezoelectric elements 6a and 6b to the optical fiber 5.

Figure 3:
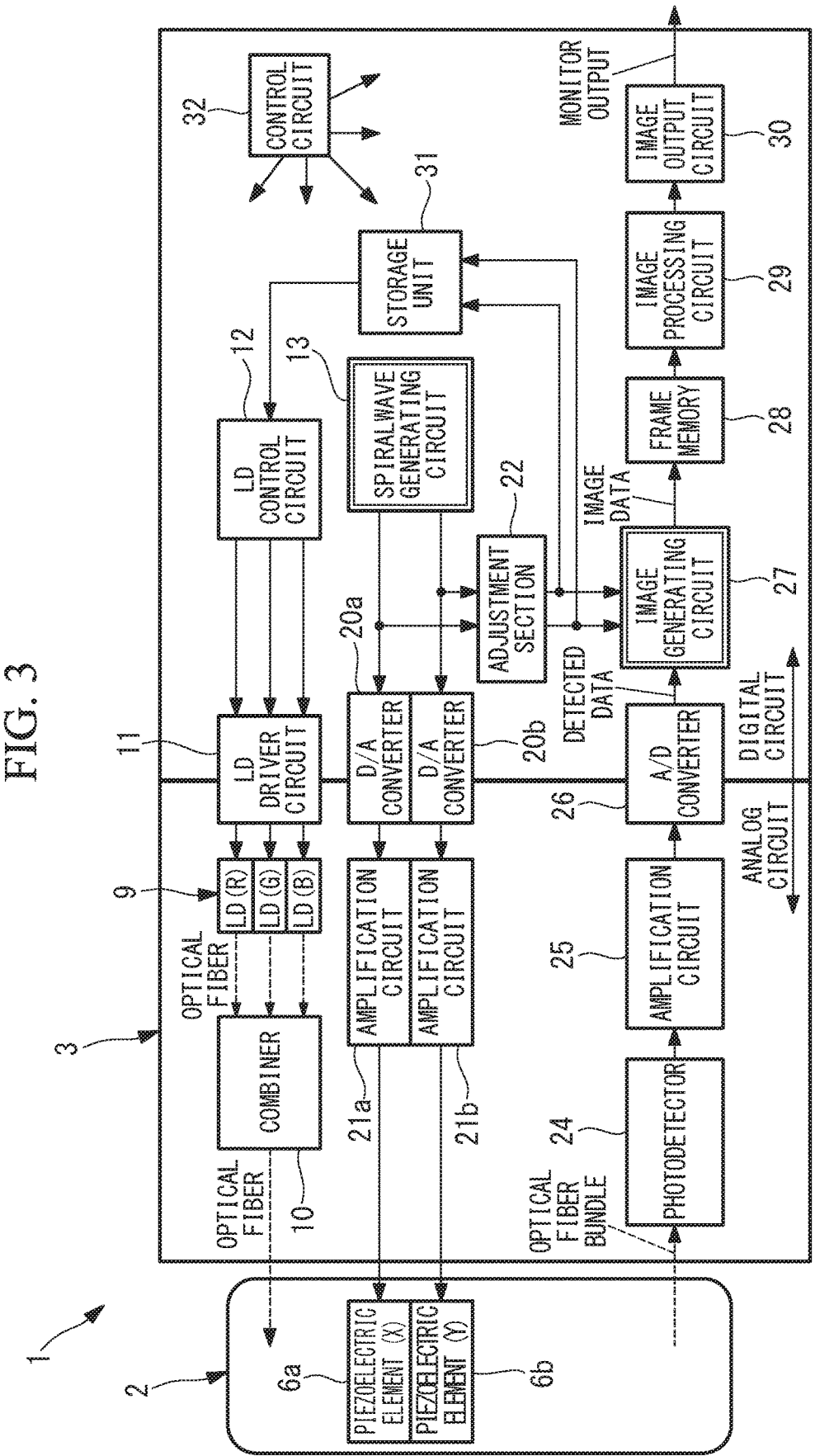
FIG. 3 is a block diagram illustrating the scanning-type image acquisition device in FIG. 1.

The endoscope control device 3, as illustrated in FIG. 3, includes the light source 9 composed of three color (R, G, B) laser diodes (LDs) and a combiner 10 that combines the waves of the illumination light from the light source 9 and makes them incident on the optical fiber 5 of the scanning-type endoscope 2. In addition, the endoscope control device 3 includes an LD driver circuit 11 for generating drive signals for the respective LDs and an LD control circuit (control unit) 12 that controls the LD driver circuit 11.

Figure 4:
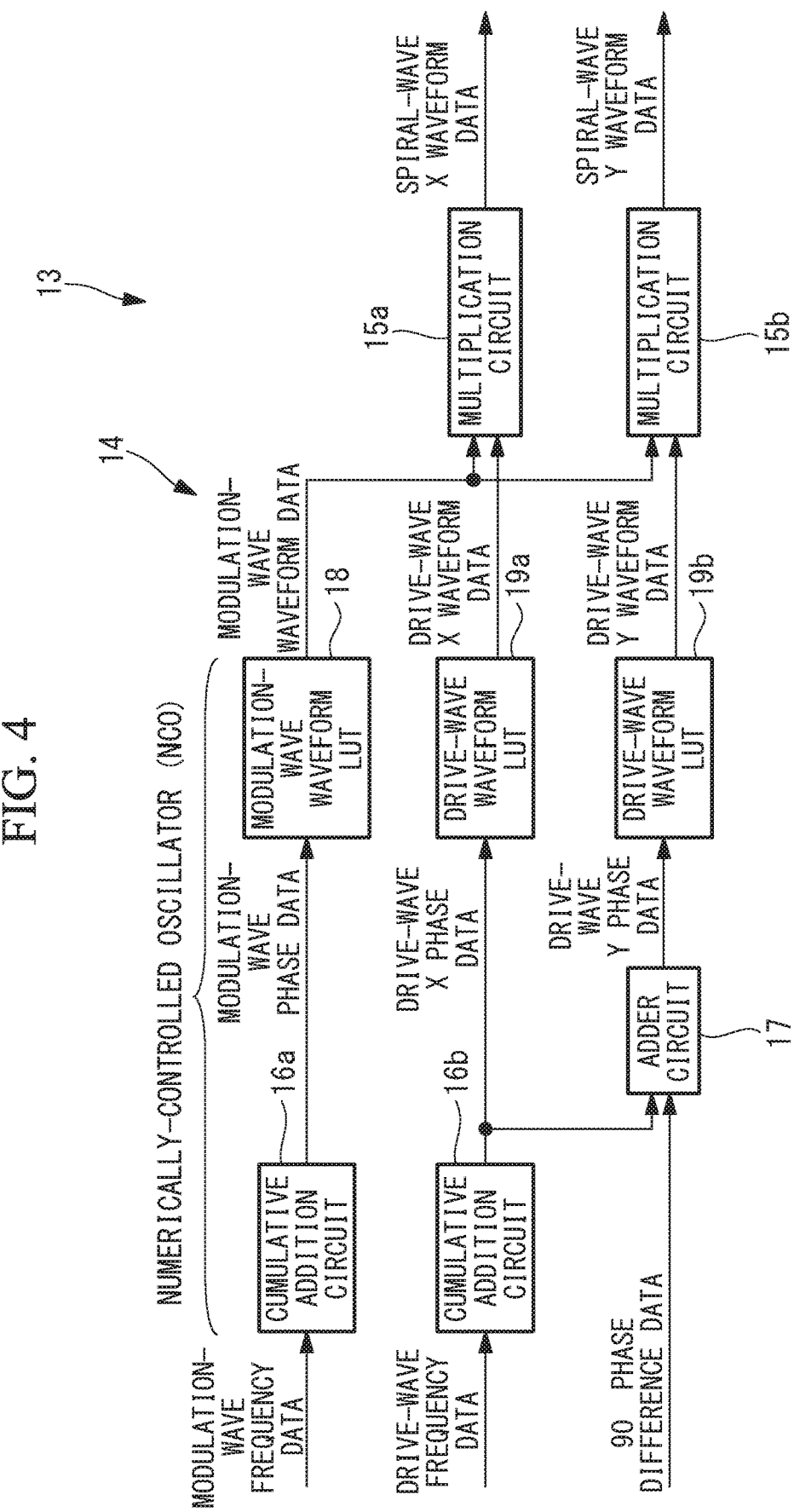
FIG. 4 is a block diagram illustrating a spiral-wave generating circuit provided in the scanning-type image acquisition device in FIG. 1.
Figure 5:
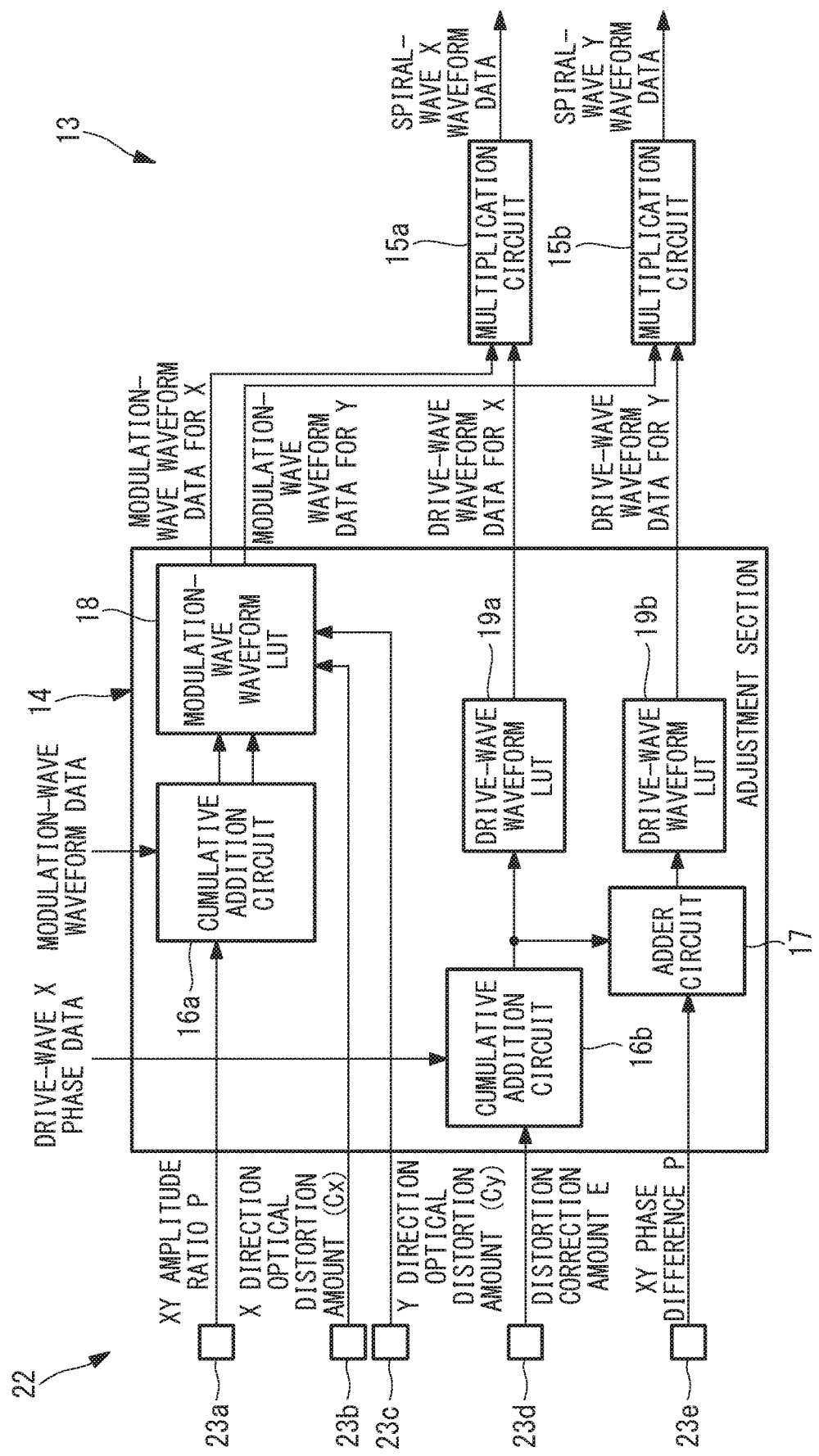
FIG. 5 is a block diagram illustrating a spiral-wave generating circuit and an adjustment section in FIG. 4.

In addition, the endoscope control device 3 includes a spiral-wave generating circuit (drive-signal generating circuit) 13 that generates drive signal waveform data that causes the piezoelectric elements 6a and 6b of the scanning-type endoscope 2 to vibrate. The spiral-wave generating circuit 13, as illustrated in FIGS. 4 and 5, includes a numerically controlled oscillator (NCO) 14, which generates waveform data that causes the optical fiber 5 to vibrate in the x direction and waveform data that causes the optical fiber 5 to vibrate in the y direction, and multiplication circuits 15a and 15b. The NCO 14 includes cumulative addition circuits 16a and 16b, an adder circuit 17, a modulation-waveform lookup table (LUT) 18, and drive-wave waveform LUTs 19a and 19b, and is configured to generate drive waves that draw a circular orbit in the xy plane and modulation waves that modulate the radius of the drive waves, respectively.

Then, the endoscope control device 3 multiplies the drive wave in the x direction by the modulation wave by using the multiplication circuit 15a to generate the spiral-wave x waveform data, and multiplies the drive wave in the y direction by the modulation wave by using the multiplication circuit 15b to generate spiral-wave y waveform data. The generated spiral-wave x waveform data is converted into a voltage by a D/A converter 20a, which is then amplified by an amplification circuit 21a and inputted to the piezoelectric element 6a that generates vibration in the x direction. In addition, the spiral-wave y waveform data generated by the multiplication circuit 15b is also converted into a voltage by a D/A converter 20b, which is then amplified by an amplification circuit 21b and inputted to the piezoelectric element 6b that generates vibration in the y direction.

In addition, the endoscope control device 3 includes an adjustment section 22 that generates position reference data from drive-wave x phase data and modulation-wave waveform data output from the spiral-wave generating circuit 13.

As illustrated in FIG. 5, the adjustment section 22 includes five adjustment operation units 23a, 23b, 23c, 23d, and 23e that are adjusted manually, and is configured to generate position reference data by adjusting drive-wave phase data and the modulation-wave waveform data on the basis of amounts of adjustment input by using the adjustment operation units 23a, 23b, 23c, 23d, and 23e.

More specifically, as illustrated in FIG. 5, the adjustment section 22 is configured to enable input of five amounts of adjustment of an XY amplitude ratio R, an x-direction optical distortion amount Cx, a y-direction optical distortion amount Cy, a distortion correction amount E, and an XY phase difference P via the adjustment operation units 23a, 23b, 23c, 23d, and 23e, respectively.

The XY amplitude ratio R is an adjustment value for adjusting the ratio between modulation wave x and y wave height values, and adjustment is performed by dividing the modulation-wave waveform data outputted from the spiral-wave generating circuit 13 for x and y and adjusting each amplitude by a factor corresponding to the inputted amount of adjustment.

In addition, although the optical distortions Cx and Cy are generated by the illumination lens 7, the optical distortions Cx and Cy are determined from the distance from the center of the scanning trajectory and therefore are calculated from the radius of the spiral shape. That is, it is sufficient that adjustment of the modulation wave be performed. The amount of adjustment can be calculated by the function in equation (1).

$$Hx = \frac{(Cx \cdot hx)}{\sqrt{f^2 - (Cx \cdot hx)^2}} \quad \text{\{Equation 1\}}$$

$$Hy = \frac{Cy \cdot hy}{\ldots Cy \cdot hy}$$

Here,
Cx: adjustment coefficient of the optical distortion amount in the x direction,
Cy: adjustment coefficient of the optical distortion amount in the y direction,
Hx: modulation-wave waveform data after conversion in x direction,
Hy: modulation-wave waveform data after conversion in y direction,
hx: modulation-wave waveform data before modulation in x direction,
hy: modulation-wave waveform data before modulation in y direction,
f: focal length of the illumination lens 7.

In addition, the distortion correction amount E can be calculated by the following equation (2) as a phase shift for each cycle of the spiral waves x and y for driving the piezoelectric elements 6a and 6b in the spiral shape of the scanning trajectory of the illumination light.

$$\text{OUTWARD PATH}: \Delta\theta(n) = E \cdot \frac{\sin\left(\frac{2\pi}{N} \cdot n\right)}{\frac{1}{2}\left\{1 - \cos\left(\frac{2\pi}{N} \cdot n\right)\right\}} \quad \text{\{Equation 2\}}$$

$$\text{RETURN PATH}: \Delta\theta(n) = E \cdot \frac{-\sin\left(\frac{2\pi}{N}(N - n)\right)}{\frac{1}{2}\left\{1 - \cos\left(\frac{2\pi}{N}(N - n)\right)\right\}}$$

Here,
E: adjustment coefficient of distortion correction amount,
n: number of cycles of drive wave in outward path (or return path)
N: total number of cycle of drive wave in outward path (or return path)
Δθ(n): phase shift in cycle number n.

By adding the phase shift Δθ(n) to the drive-wave phase data, it is possible to adjust the phase shift for each cycle, and by increasing or decreasing the adjustment coefficient E of the distortion correction amount in accordance with the degree of phase shift, it is possible to adjust the phase change amount.

The XY phase difference adjustment adjusts the phase difference P between x and y of the drive waves, and in order to calculate the drive-wave phase data for y, the phase difference between both waves is added to the drive-wave phase data for x. Adjustment can be carried out by increasing or decreasing the phase difference data to be added.

In addition, the endoscope control device 3, as illustrated in FIG. 2, includes a photodetector (photodetection unit) 24 that detects light that has been scattered by the subject and received by the fiber bundle 8 of the scanning-type endoscope 2, an amplification circuit 25 that amplifies the scattered light detected by the photodetector, an A/D converter 26 that converts the intensity value of the amplified scattered light into a digital signal, and an image generating circuit (image generating unit) 2/that generates an image by arranging the intensity values of the converted scattered light in accordance with position reference data output from the adjustment section 22. The generated image is configured to be output to the monitor 4 via a frame memory 28 that stores the image, an image processing circuit 29 that performs image processing, and an image output circuit 30, and displayed thereon.

In addition, the endoscope control device 3 includes a storage unit 31 that stores, in a switchable manner, a plurality of tables in which coordinates of projection graphic data and luminance are associated with each other. The tables in the storage unit 31 are configured so as to be switchable by a command signal from a control circuit 32. The control circuit 32 is configured to control each unit in the endoscope control device 3.

One table is a table for illumination in which the luminances of all the coordinates are kept constant, and is configured such that all scanning positions generated by the spiral-wave generating circuit 13 are illuminated by illumination light of the same luminance.

Figure 6:
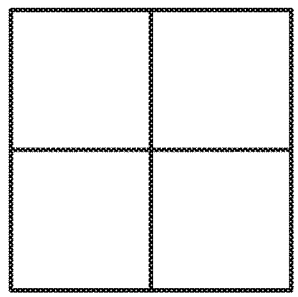
FIG. 6 is a diagram illustrating an example of a projection graphic stored in a calibration look-up table stored in a storage unit of the scanning-type image acquisition device in FIG. 1.

For example, as illustrated in FIG. 6, another table is a table for calibration in which the luminance of predetermined coordinates is increased so as to project a grid-shaped projection graphic composed of 2×2=4 squares.

The operation of the scanning-type image acquisition device 1 according to the present embodiment thus configured will be described below.

In the scanning-type image acquisition device 1 according to the present embodiment, when the control circuit 32 selects a calibration table and operates the spiral-wave generating circuit 13, the piezoelectric element 6a in the x direction and the piezoelectric element 6b in the y direction are driven by using the generated spiral-wave x waveform data and spiral-wave y waveform data, and the tip 5a of the optical fiber 5 is vibrated spirally.

In addition, from the modulation-wave waveform data and the drive-wave x phase data output from the spiral-wave generating circuit 13, position adjustment data is generated by the adjustment section 22 and sent to the image generating circuit 27 and the storage unit 31. Because the calibration table is selected in the storage unit 31, when, among the coordinates corresponding to the position reference data and the calibration table, the position reference data is arranged at coordinates where the luminance values exist in the table, the light source 9 is turned on by the LD control circuit 12 and illuminates the subject from the tip 5a of the optical fiber 5.

In the case where the spiral-wave x waveform data and the spiral-wave y waveform data match the position reference data for x and y output from the adjustment section 22, a graphic having a shape matching the graphic data stored in the table is projected onto the subject; however, in the case where the spiral waveform is distorted due to individual differences between the piezoelectric elements 6a and 6b and the like, the projection graphic projected on the subject is also distorted.

In the present embodiment, while the user views the projection graphic projected on the subject, by operating the five adjustment operation units 23a, 23b, 23c, 23d, and 23e provided in the adjustment section 22, the user adjusts each amount of adjustment so that the subject matches the graphic data stored in the table.

Figure 7:
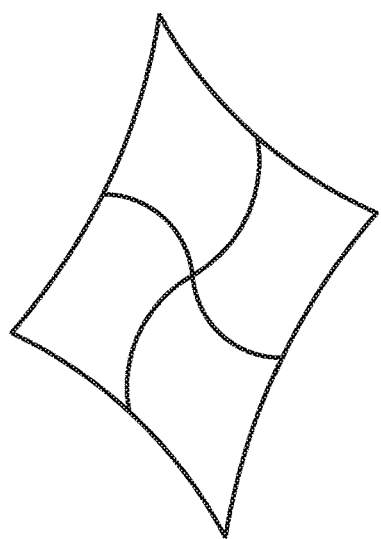
FIG. 7 is a diagram illustrating an example of a case where the projection graphic in FIG. 6 is projected onto a subject.

That is, in the case where the graphic data illustrated in FIG. 6 is stored, when a horizontally elongated projection graphic as illustrated in FIG. 7 is projected onto a subject composed of a plane arranged perpendicularly to the projection optical axis, the user operates the adjustment operation unit 23a for the XY amplitude ratio R in order to adjust the aspect ratio of the projection graphic. As a result, as illustrated in FIG. 8, it is possible to perform adjustment so that the aspect ratios of the two center lines Lx and Ly passing through the center of the projection graphic become equal.

Figure 8:
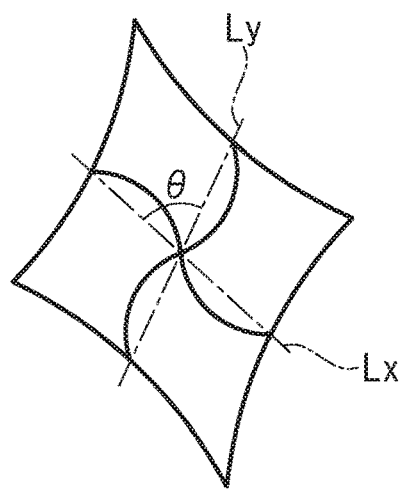
FIG. 8 is a diagram illustrating a state in which an aspect ratio of the projection graphic in FIG. 7 is corrected.

Next, as illustrated in FIG. 8, when the angle θ formed by the two center lines Lx and Ly intersecting at the center of the projection graphic system is not 90°, the user operates the adjustment operation unit 23e for the XY phase difference P. As a result, as illustrated in FIG. 9, adjustment can be made so that the two center lines Lx and Ly are perpendicular to each other (θ=90°).

Figure 9:
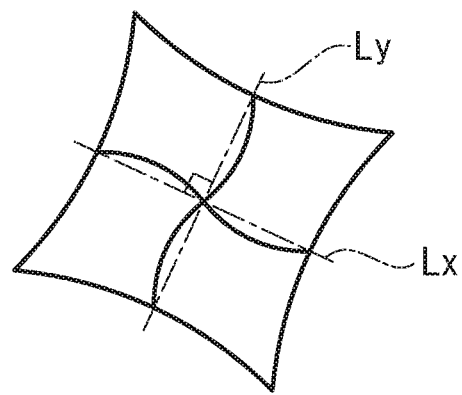
FIG. 9 is a diagram illustrating a state in which a relative angle of a center line of the projection graphic in FIG. 8 is corrected to 90°.

Next, as illustrated in FIG. 9, in the case where two lines intersecting at the center of the projection graphic are each curved in one direction, the user operates the adjustment operation unit 23d for the distortion correction amount E. As a result, as illustrated in FIG. 10, it is possible to perform adjustment so that the two lines are each straight.

Figure 10:
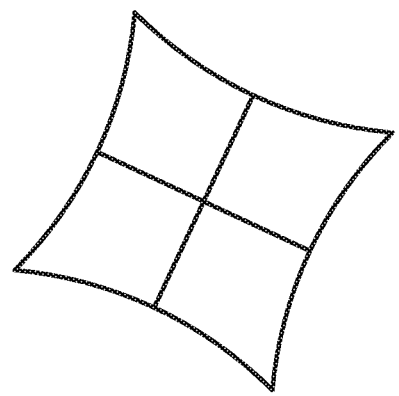
FIG. 10 is a diagram illustrating a state in which distortion of the center line of the projection graphic in FIG. 9 is corrected.
Figure 11:
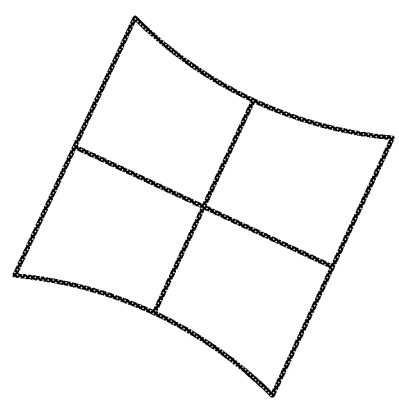
FIG. 11 is a diagram illustrating a state in which distortion of the x-direction outermost lines of the projection graphic in FIG. 10 is corrected.
Figure 12:
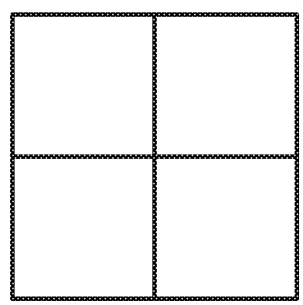
FIG. 12 is a diagram illustrating a state in which distortion of the y-direction outermost lines of the projection graphic in FIG. 11 is corrected.

As illustrated in FIG. 10, in the case where the outermost lines of the projection graphic are curved, the user operates the adjustment operation units 23b and 23c for the adjustment coefficient Cx of the optical distortion amount in the x direction and the adjustment coefficient Cy of the optical distortion amount in the y direction. As a result, as illustrated in FIGS. 11 and 12, it is possible to adjust the lines arranged at the outermost circumferential position so as to be straight.

That is, according to the scanning-type image acquisition device 1 according to the present embodiment, by merely adjusting the amount of adjustment so that the projection graphic projected on the subject matches the graphic data stored in the calibration table, there is an advantage that the distortion of the observation image due to individual differences and the like of the piezoelectric elements 6a and 6b can be corrected. In this case, there is no need for the user to prepare a subject such as a reference image, and there is an advantage that the adjustment can be easily performed.

Once the amounts of adjustment have been set, by using the setting amounts as is, it is possible to acquire an observation image without distortion as long as the vibration trajectory of the tip 5a of the optical fiber 5 does not change with time.

Further, in the present embodiment, although a grid-shaped projection graphic composed of four squares has been exemplified as an image to be projected on a subject in order to adjust position reference data, instead of this, another projection graphic such as a grid-shaped projection graphic composed of 16 squares may be adopted.

In addition, the projection graphic is not limited to a grid shape, and any projection graphic may be used as long as it includes two line segments perpendicular to each other at the center and at least one line segment not passing through the center.

The two line segments perpendicular to each other at the center can be used to check the XY amplitude ratio R, the XY phase difference P, and the distortion correction amount E. In addition, the line segment that does not pass through the center can be used to check the optical distortion amounts Cx and Cy.

Figure 13:
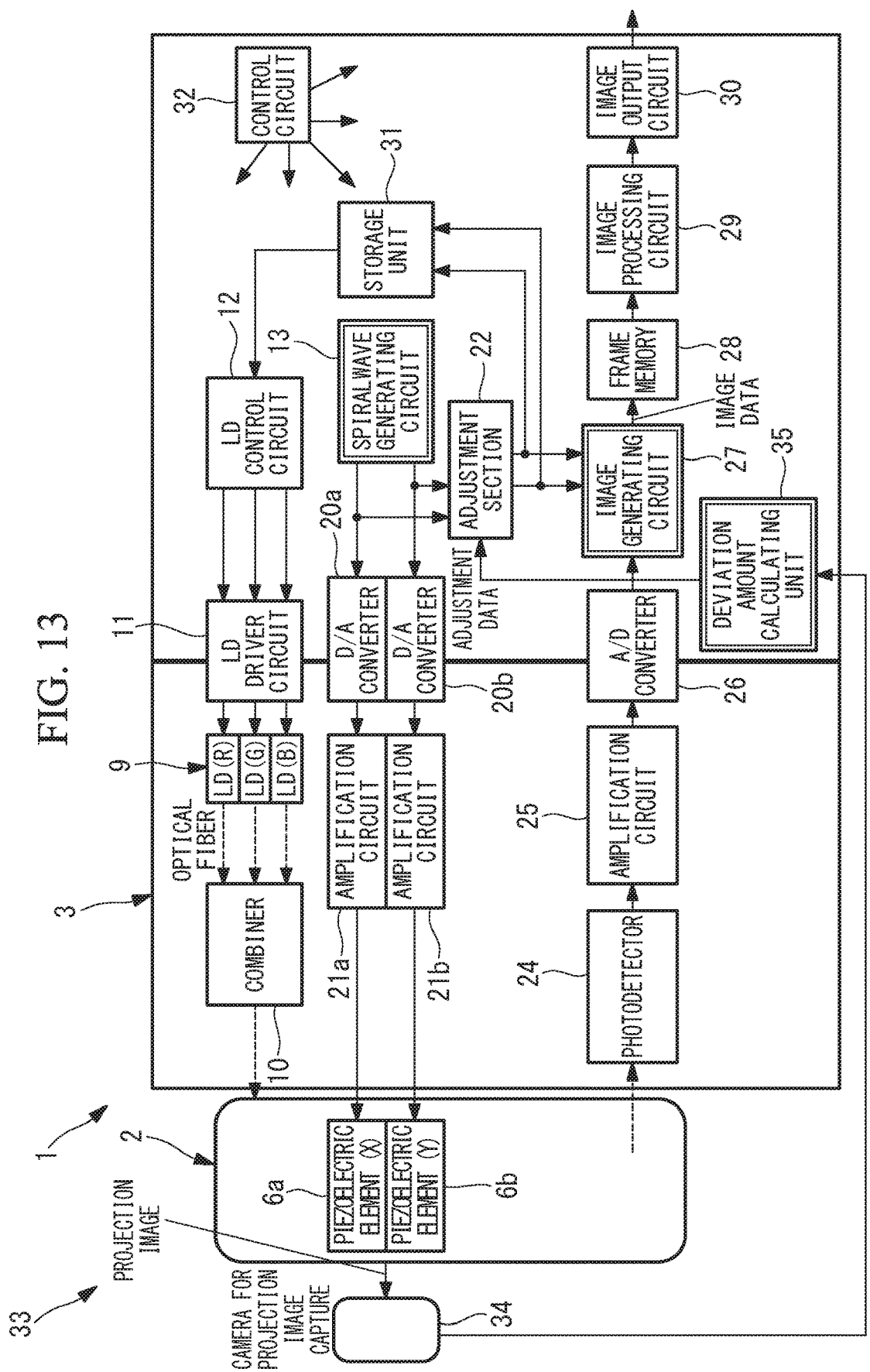
FIG. 13 is a block diagram illustrating a scanning-type image acquisition system according to an embodiment of the present invention.

In addition, in the present embodiment, although the five amounts of adjustment are adjusted by the adjustment operation units 23a, 23b, 23c, 23d, and 23e provided in the adjustment section 22, instead of this, as illustrated in FIG. 13, a scanning-type image acquisition system 33 including a camera (imaging unit) 34 that captures a projection image projected onto a subject may be adopted.

In the scanning-type image acquisition system 33, the endoscope control device 3 may include a deviation amount calculating unit (adjustment amount determining unit) 35 that compares the projection image acquired by the camera 34 with the projection graphic data in the calibration lookup table stored in the storage unit 31 and calculates an amount of deviation, and the adjustment section 22 may adjust the position reference data on the basis of the deviation amount calculated by the deviation amount calculating unit 35.

By doing so, there is an advantage that the adjustment of the amounts of adjustment can be automated.

Further, the amounts of adjustment can be stored in either the adjustment section 22 or the deviation amount calculating unit 35.

Figure 14A:
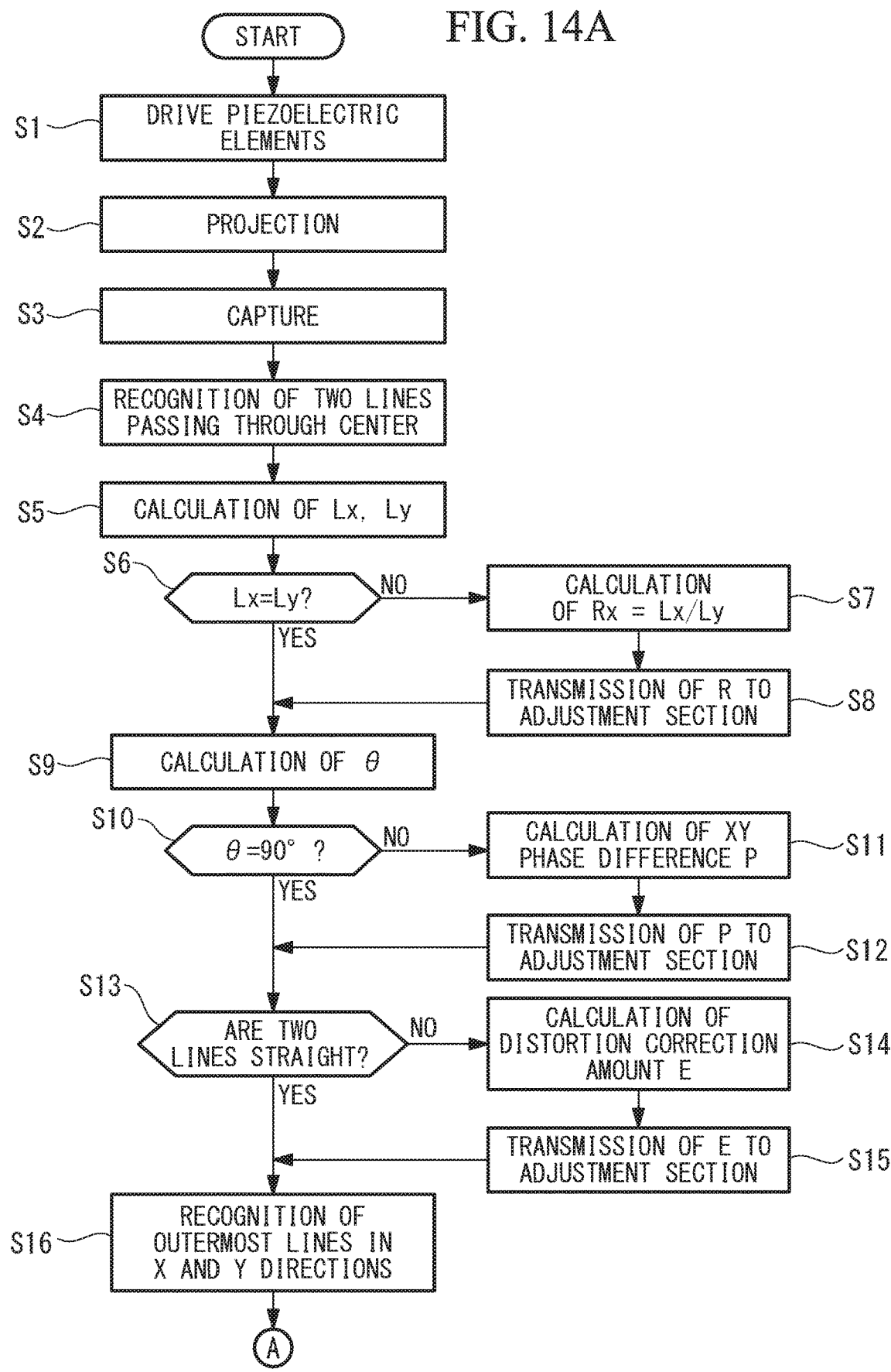
FIG. 14A is a flowchart illustrating a calibration procedure of the scanning image acquisition system in FIG. 13.
Figure 14B:
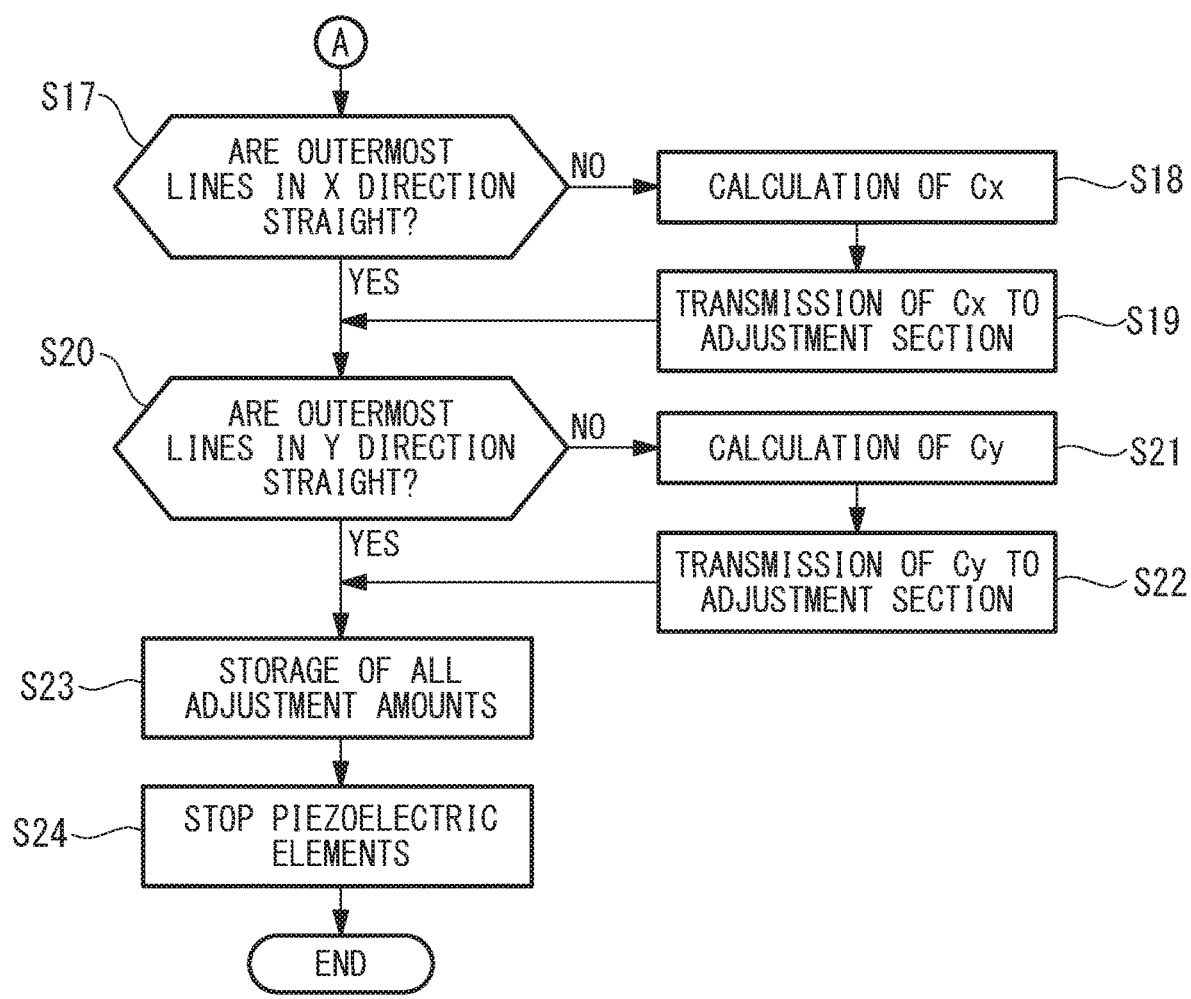
FIG. 14B is a flowchart illustrating the calibration procedure from A in FIG. 14A.

That is, the operation of the scanning-type image acquisition system 33 according to the present embodiment is as illustrated in the flowcharts in FIGS. 14A and 14B.

First, when the piezoelectric elements 6a and 6b are driven and calculation of the spiral waves x and y is started (step S1), a calibration look-up table is selected, and projection of a projection graphic for calibration is performed (step S2). The projected projection graphic is captured by the camera 34 (step S3), the image of the acquired projection graphic is subjected to image processing in the deviation amount calculating unit 35, two center lines passing through the center are recognized (step S4), and distances Lx and Ly between both ends of each center line are calculated (step S5).

Next, the deviation amount calculating unit 35 determines whether or not the distances Lx and Ly are equal (step S6) and, in the case where they are not equal to each other, the XY amplitude ratio R=Lx/Ly is calculated (step S7) and transmitted to the adjustment section 22 (step S8).

In the case where the distances Lx and Ly are equal and after the XY amplitude ratio R has been transmitted to the adjustment section 22, the deviation amount calculating unit 35 calculates the angle θ formed by two straight lines, each straight line connecting both ends of a corresponding center line (step S9).

Then, it is determined whether or not the angle θ is 90° (step S10), and in the case where it is not 90°, the XY phase difference P is calculated (step S11) and transmitted to the adjustment section 22 (step S12).

In the case where the angle θ is 90° and after the XY phase difference P has been transmitted to the adjustment section 22, the deviation amount calculating unit 35 determines whether or not the two center lines are straight (step S13), and the distortion correction amount E is calculated (step S14) and transmitted to the adjustment section 22 (step S15).

In the case where the two center lines are straight and after the distortion correction amount E has been transmitted to the adjustment section 22, the deviation amount calculating unit 35 recognizes the outermost lines in the x direction and the y direction (step S16), determines whether or not the outermost lines in the x direction are straight lines (step S17), and, in the case where they are not straight lines, the x-direction optical distortion amount Cx is calculated (step S18) and transmitted to the adjustment section 22 (step S19).

In the case where the outermost lines in the x direction are straight lines and after the x direction optical distortion amount Cx has been transmitted to the adjustment section 22, the deviation amount calculating unit 35 determines whether or not the outermost lines in the y direction are straight lines (step S20) and, in the case where they are not straight lines, the y-direction optical distortion amount Cy is calculated (step S21) and transmitted to the adjustment section 22 (step S22).

In the case where the outermost lines in the y direction are straight lines and after the y direction optical distortion amount Cy has been transmitted to the adjustment section 22, the adjustment section 22 stores all sent amounts of adjustment (step S23), the piezoelectric elements 6a and 6b are stopped (step S24), and the calibration operation is completed.

Further, the calculation order of the amounts of adjustment in the above is arbitrary, and the amounts may be calculated at the same time and transmitted to the adjustment section 22.

Further, the present invention is not limited to the above-described embodiments and can be appropriately changed without departing from the gist of the present invention. For example, instead of the piezoelectric elements 6a and 6b, drivers using permanent magnets and electromagnetic coils may be adopted. In addition, although the piezoelectric elements 6a and 6b are fixed to the optical fiber 5 via the ferrule 40, it is also possible to use a structure in which the piezoelectric elements 6a and 6b are directly fixed to the optical fiber 5.

As a result, the above-described embodiment also leads to the following aspects.

An aspect of the present invention provides a scanning-type image acquisition device that includes: driving units that respectively vibrate in an x direction and a y direction that are perpendicular to the longitudinal axis of an optical fiber that guides illumination light from a light source and cause a tip of the optical fiber to be spirally scanned on a subject, a drive-signal generating unit for generating drive signals for driving the driving units, an adjustment section that adjusts the drive signals generated by the drive-signal generating unit and generates position reference data, a photodetection unit that detects scattered light of the illumination light at each subject scanning position of an illumination light spot by the driving units; and an image generating unit that generates an image by arranging intensity values of the scattered light detected by the photodetection unit in pixels in accordance with the position reference data output from the adjustment section.

According to this aspect, when the driving units are driven using the drive signals generated by the drive-signal generating unit, the tip of the optical fiber is vibrated in two directions perpendicular to the longitudinal axis thereof, and an illumination light spot emitted from the tip of the optical fiber is spirally scanned on the subject. At each scanning position of the subject, scattered light is generated by illumination of the illumination light and detected by the photodetection unit. An image is generated by arranging the intensity values of the detected scattered light in pixels in accordance with the position reference data.

In this case, since the position reference data is generated by the adjustment section through adjustment of the drive signals, even if the trajectory of the illumination light spot anticipated from the drive signals is different from the actual trajectory of the illumination light spot, it is possible to adjust the position reference data so as to make the trajectories match, and it is possible to perform calibration easily with high accuracy and without preparing a calibration pattern image as a subject.

In the above aspect, the drive-signal generating unit may generate the drive signals by multiplying a drive wave in the x direction and a drive wave in the y direction, which form a circular orbit on the xy plane, and modulation waves that modulate radius of the drive waves, respectively, and input the drive signals to the driving units.

By doing so, it is possible to easily vibrate the tip of the optical fiber spirally.

In addition, in the above-described aspect, the adjustment section may adjust an amplitude ratio between the modulation waves in the x direction and the y direction.

By doing so, it is possible to improve the ellipticity of the spiral trajectory of the illumination light spot on the subject.

In addition, in the above aspect, the adjustment section may adjust the phase difference between the drive waves in the x direction and the y direction.

By doing so, it is possible to improve the ellipticity of the spiral trajectory of the illumination light spot on the subject.

In addition, in the above-described aspect, the adjustment section may adjust a phase change for each cycle of the drive waves in the x direction and the y direction.

By doing so, it is possible to improve the amount of twist of the spiral trajectory of the illumination light spot on the subject.

In addition, in the above-described aspect, an optical lens that transmits the illumination light emitted from the tip of the optical fiber may be provided, and the adjustment section may adjust the waveform of the modulation waves on the basis of the focal length of the optical lens.

By doing so, it is possible to improve the optical distortion amount of the spiral trajectory of the illumination light spot on the subject.

In addition, in the above-described aspect, a storage unit that stores a table in which coordinates of projection graphic data are associated with luminance and a control unit that controls light emission timing of the light source in accordance with the luminance of coordinates corresponding to the position reference data adjusted by the adjustment section and the table may be provided.

By doing so, the control unit controls the light emission timing of the light source in accordance with the luminance of coordinates corresponding to the position reference data adjusted by the adjustment section and the table so that the projection graphic corresponding to the projection graphic data is projected onto the subject. By adjusting the amounts of adjustment by the adjustment section while viewing the projected projection graphic, it is possible to make the projection graphic projected on the subject match the projection graphic data. Thereby, it is possible to easily and accurately perform calibration without preparing a calibration pattern image as a subject.

In addition, according to another aspect of the present invention, there is provided an image processing device including the scanning-type image acquisition device, an imaging unit configured to capture a projection graphic projected by the scanning-type image acquisition device, and an adjustment amount determining unit that determines an amount of adjustment by the adjustment section on the basis of an amount of deviation from the projection graphic data.

According to this aspect, the projection graphic system projected onto the subject is captured by the imaging unit, the amount of deviation from the projection graphic data is obtained, and the adjustment amount determining unit determines the amount of adjustment by the adjustment section. As a result, it is possible to generate position reference data that can project a projection graphic that matches the projection graphic data, and easily and precisely perform calibration without preparing a calibration pattern image as a subject.

According to the present invention, it is possible to easily and precisely perform calibration without preparing a calibration pattern image as a subject.

REFERENCE SIGNS LIST 1 scanning-type image acquisition device
5 optical fiber
6a, 6b piezoelectric element (driver)
7 illumination lens (optical lens)
9 light source
12 LD control circuit (controller)
13 spiral-wave generating circuit (drive-signal generating circuit)
22 adjustment section
24 photodetector
27 image generating circuit
31 storage unit
33 scanning-type image acquisition system
34 camera
35 deviation amount calculation section (calculator)
P phase difference
R amplitude ratio

The invention claimed is:

1. A scanning-type image acquisition device comprising:
drivers that respectively vibrate in an x direction and in a y direction, the drivers being perpendicular to a longitudinal axis of an optical fiber that guides illumination light from a light source, the drivers being configured to cause a tip of the optical fiber to be spirally scanned on a subject;
a photodetector that detects scattered light of the illumination light at each scanning position of an illumination light spot on the subject due to the drivers; and
a controller configured to:
generate drive signals for driving the drivers;
adjust the generated drive signals and generate position reference data;
generate an image by arranging intensity values of the detected scattered light in pixels in accordance with the generated position reference data;
control retrieving of data from a table in which the coordinates of projection graphic data and luminance are associated with each other; and
control a light emission timing of the light source in accordance with the luminance of coordinates corresponding to the adjusted position reference data and the table.

2. The scanning-type image acquisition device according to claim 1, wherein the controller generates the drive signals by multiplying a drive wave in an x direction and a drive wave in a y direction, which form a circular orbit on an xy plane, and modulation waves for modulating radius of the drive waves, respectively, and inputs the drive signals to the drivers.

3. The scanning-type image acquisition device according to claim 2, wherein the controller adjusts an amplitude ratio between the modulation waves in the x direction and the y direction.

4. The scanning-type image acquisition device according to claim 2, wherein the controller adjusts a phase difference between the drive waves in the x direction and the y direction.

5. The scanning-type image acquisition device according to claim 2, wherein the controller adjusts a phase change for each cycle of the drive waves in the x direction and the y direction.

6. The scanning-type image acquisition device according to claim 2, further comprising an optical lens that transmits the illumination light emitted from the tip of the optical fiber, wherein the controller adjusts waveforms of the modulation waves based on a focal length of the optical lens.

7. A scanning-type image acquisition system comprising:
the scanning-type image acquisition device according to claim 1, and
a camera that captures a projection graphic projected by the scanning image acquisition device,
wherein the controller calculates a deviation amount between the projection graphic acquired by the camera and the projection graphic data to determine an amount of the adjustment.

8. A scanning-type image acquisition device comprising:
a controller configured to:
generate drive signals for controlling drivers that respectively vibrate in an x direction and in a y direction to cause a tip of an optical fiber to be spirally scanned on a subject, the optical fiber guiding illumination light from a light source;
control detection of scattered light of the illumination light at each scanning position of an illumination light spot on the subject due to the drivers;
adjust the generated drive signals and generate position reference data;
generate an image by arranging intensity values of the detected scattered light in pixels in accordance with the generated position reference data;
control retrieving of data from a table in which the coordinates of projection graphic data and luminance are associated with each other; and
control a light emission timing of the light source in accordance with the luminance of coordinates corresponding to the adjusted position reference data and the table.

\* \* \* \* \*